(12) United States Patent
Snyder

(10) Patent No.: US 9,168,385 B2
(45) Date of Patent: Oct. 27, 2015

(54) EXTERNAL DEFIBRILLATOR WITH SHOCK ACTIVATED BY CESSATION OF PRECORDIAL COMPRESSIONS

(75) Inventor: David Snyder, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 3286 days.

(21) Appl. No.: 10/537,792

(22) PCT Filed: Dec. 5, 2003

(86) PCT No.: PCT/IB03/05812
§ 371 (c)(1),
(2), (4) Date: Jun. 6, 2005

(87) PCT Pub. No.: WO2004/054656
PCT Pub. Date: Jul. 1, 2004

(65) Prior Publication Data
US 2006/0116724 A1    Jun. 1, 2006

Related U.S. Application Data

(60) Provisional application No. 60/433,375, filed on Dec. 13, 2002, provisional application No. 60/476,981, filed on Jun. 9, 2003.

(51) Int. Cl.
| | |
|---|---|
| *A61N 1/00* | (2006.01) |
| *A61B 5/04* | (2006.01) |
| *A61H 31/00* | (2006.01) |
| *A61N 1/39* | (2006.01) |
| *A61B 5/0428* | (2006.01) |
| *A61B 5/046* | (2006.01) |
| *A61B 5/00* | (2006.01) |

(52) U.S. Cl.
CPC ............... *A61N 1/39* (2013.01); *A61B 5/0428* (2013.01); *A61B 5/7203* (2013.01); *A61B 5/7207* (2013.01); *A61N 1/3925* (2013.01); *A61B 5/046* (2013.01); *A61B 5/726* (2013.01)

(58) Field of Classification Search
USPC .................................. 607/5; 600/509; 601/41
See application file for complete search history.

(56) References Cited

U.S. PATENT DOCUMENTS

| | | | | |
|---|---|---|---|---|
| 4,588,383 | A * | 5/1986 | Parker et al. ................... | 434/265 |
| 4,610,254 | A * | 9/1986 | Morgan et al. .................... | 607/6 |
| 4,619,265 | A * | 10/1986 | Morgan et al. .................... | 607/6 |
| 4,928,674 | A * | 5/1990 | Halperin et al. ................. | 601/44 |
| 5,077,667 | A * | 12/1991 | Brown et al. ..................... | 607/5 |

(Continued)

FOREIGN PATENT DOCUMENTS

| | | | | |
|---|---|---|---|---|
| DE | 4243889 A1 * | 7/1993 | ........... | A61B 5/0432 |
| EP | 1 079 310 A | 2/2001 | | |
| WO | WO 02 072197 A | 9/2002 | | |

*Primary Examiner* — Nicole F Lavert

(57) ABSTRACT

A defibrillator having a pair of electrodes for delivering an artifact-compensated defibrillation shock and a method thereof is provided. The defibrillator can be deployed rapidly while administering a cardio-pulmonary resuscitation (CPR) on the patient. Upon detection of an end of the CPR operation, a correlation signal indicative of signal corruption is detected and analyzed rapidly to determine an appropriate energy level discharged across the pair of electrodes. Thereafter, a notification signal is sent to the user of the defibrillator prior to delivering the defibrillation shock to the patient. The artifact-compensated defibrillation shock is delivered if for a predetermined period of time no movements is detected.

17 Claims, 4 Drawing Sheets

(56) References Cited

U.S. PATENT DOCUMENTS

| | | | |
|---|---|---|---|
| 5,474,574 A * | 12/1995 | Payne et al. | 607/7 |
| 5,496,257 A * | 3/1996 | Kelly | 601/41 |
| 5,611,815 A * | 3/1997 | Cole et al. | 607/5 |
| 5,674,253 A * | 10/1997 | Adams et al. | 607/7 |
| 5,735,879 A * | 4/1998 | Gliner et al. | 607/7 |
| 6,125,298 A * | 9/2000 | Olson et al. | 607/5 |
| 6,171,257 B1 * | 1/2001 | Weil et al. | 600/518 |
| 6,174,295 B1 * | 1/2001 | Cantrell et al. | 601/41 |
| 6,263,238 B1 * | 7/2001 | Brewer et al. | 607/5 |
| 6,287,328 B1 | 9/2001 | Lyster et al. | |
| 6,351,671 B1 * | 2/2002 | Myklebust et al. | 607/5 |
| 6,427,083 B1 | 7/2002 | Totman et al. | |
| 6,496,731 B1 * | 12/2002 | Lovett | 607/14 |
| 6,697,671 B1 * | 2/2004 | Nova et al. | 607/5 |
| 6,827,695 B2 * | 12/2004 | Palazzolo et al. | 601/41 |
| 6,961,612 B2 * | 11/2005 | Elghazzawi et al. | 607/6 |
| 6,990,373 B2 * | 1/2006 | Jayne et al. | 607/5 |
| 7,006,865 B1 * | 2/2006 | Cohen et al. | 607/5 |
| 7,085,601 B1 * | 8/2006 | Bardy et al. | 607/5 |
| 7,089,055 B2 * | 8/2006 | Cates et al. | 607/4 |
| 2003/0023277 A1 * | 1/2003 | Owen et al. | 607/5 |
| 2003/0088285 A1 * | 5/2003 | Marcovecchio et al. | 607/5 |
| 2003/0130697 A1 * | 7/2003 | Halperin et al. | 607/2 |
| 2003/0144699 A1 * | 7/2003 | Freeman | 607/5 |
| 2003/0195567 A1 * | 10/2003 | Jayne et al. | 607/5 |
| 2004/0162585 A1 * | 8/2004 | Elghazzawi et al. | 607/5 |
| 2007/0299354 A1 * | 12/2007 | Striepe et al. | 600/509 |

* cited by examiner

EXTERNAL DEFIBRILLATOR WITH SHOCK ACTIVATED BY CESSATION OF PRECORDIAL COMPRESSIONS

CROSS REFERENCE TO RELATED APPLICATION

This application claims the benefit of U.S. provisional application Ser. No. 60/476,981 filed Jun. 9, 2003 and of U.S. provisional application Ser. No. 60/433,375 filed Dec. 13, 2002, which are incorporated herein by reference.

The present invention relates to devices used in electrical therapy and, in particular, to a defibrillator for delivering artifact-compensated defibrillation pulses while cardio-pulmonary resuscitation (CPR) is being performed on a patient.

Medical equipment manufacturers have developed Automated Electronic Defibrillators (AEDs) to provide early defibrillation. AEDs deliver a high-amplitude current pulse, waveform, or shock to the heart in order to restore the patient's heart rhythm to a normal level. For example, FIG. 1 depicts the conventional AED 6 being applied to a cardiac arrest victim 2 by a rescuer 4. As shown in FIG. 1, a pair of defibrillation electrodes 8 is placed on anterior-anterior (AA) positions on the victim's torso for delivering the shocks. At the same time, it is also necessary to perform a cardio-pulmonary resuscitation (CPR) on the patient while delivering the defibrillation shocks in order to revive the victim from the cardiac arrest.

In treating victims of cardiac arrest with a defibrillator, it is important that the treatment be performed very rapidly as their chances of surviving the cardiac arrest decrease drastically over time following the cardiac arrest. Thus, a quick response to cardiac arrest in administering a defibrillation shock after performing the CPR precordial compressions at the rescue scene is critical. In addition to deploying a defibrillation shock rapidly as needed to improve the resuscitation benefit, measuring accurate signals in the presence of other artifact signals, such as the movement of the victim during the CPR operation, is vital when making a correct decision with respect to a patient's treatment or, for devices that use algorithms to make decisions.

With regards to the above paragraph, there are two time intervals that are of importance, only one of which is addressed by this invention. The chance of survival decreases rapidly following the loss of circulation. Consequently the time from the beginning of the arrest until the first defibrillation shock is important. This interval is important whether or not CPR is performed, but is not addressed by this particular invention. When CPR is performed, some level of circulation is restored artificially, which can improve the chances of survival. When CPR is discontinued to allow the AED to analyze the heart rhythm (via the ECG), circulation is once again stopped. A long interval between discontinuation of CPR and shock delivery will decrease the chance of survival. It is this second interval that is addressed by this invention.

Therefore, the present invention provides an improved defibrillator that is easy to use and that enables a minimally trained user to easily, rapidly, and effectively deploy the defibrillator to treat the patient, while reducing the time interval between precordial compressions and delivery of a defibrillation shock.

The present invention is directed to a method and system for quickly and accurately applying the defibrillating shock to a victim of sudden cardiac arrest following delivery of CPR precordial compressions.

A more complete understanding of the method and apparatus of the present invention is available by reference to the following detailed description when taken in conjunction with the accompanying drawings wherein.

Figure 1:
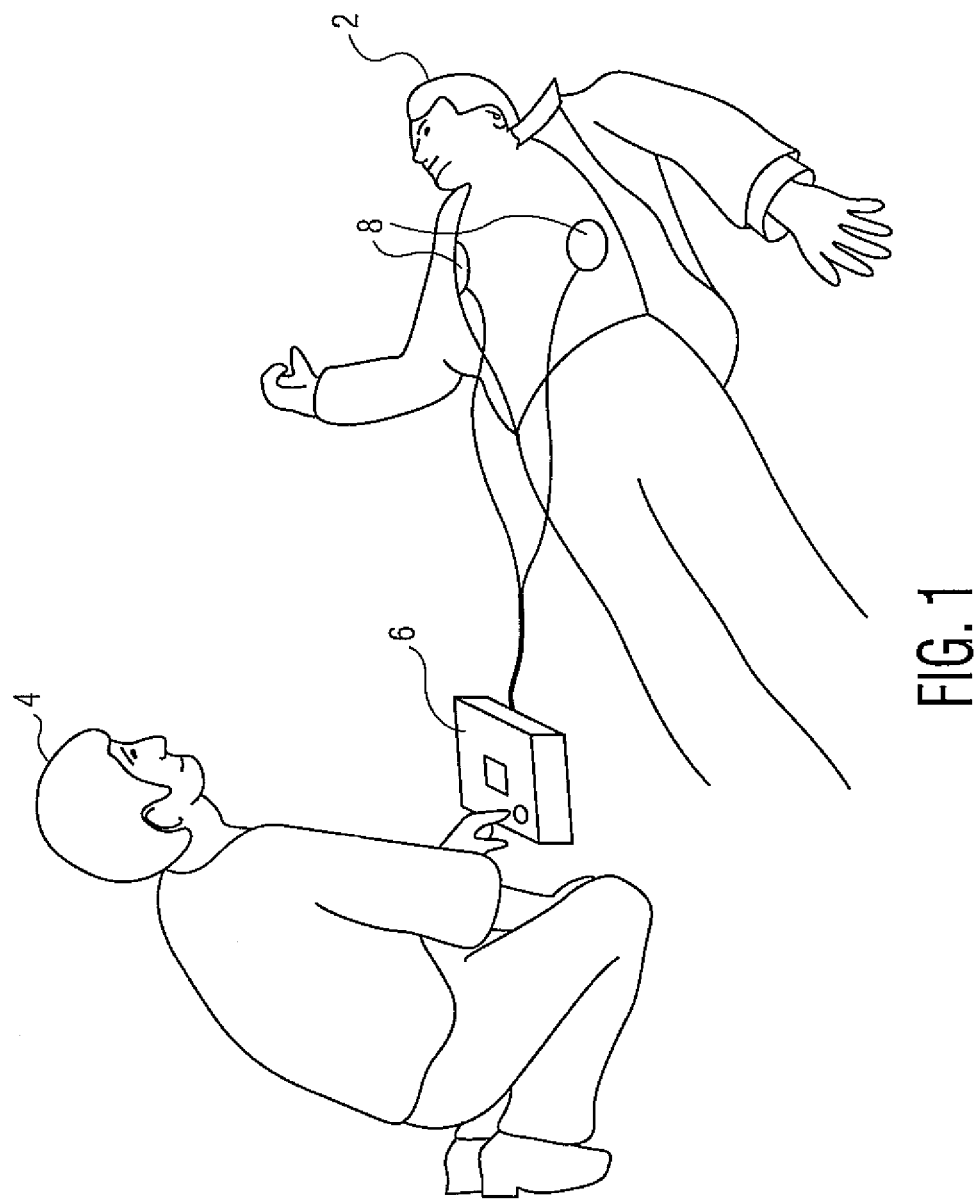
FIG. 1 is an illustration of a defibrillator being applied to a patient under cardiac arrest according to an embodiment of the present invention.

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

In the prior art system, portable automated external defibrillators do not consider the mechanical disturbance of the patient as an inhibitor/enable of shock delivery. In particular, the mechanical movement of the patient's chest is not compensated during the delivery of electrical therapy, thus producing a corrupted signal, which is measured by the defibrillator. In addition, other artifacts that corrupt the signals, including mechanical disturbances of sensors, electromagnetic interference, etc., are used to trigger the treatable shocks, thus resulting in inaccurate reading when delivering the defibrillation shock. Furthermore, prior art defibrillators have presented a shock hazard to the rescuer as the defibrillators are incapable of detecting whether the rescuer was in physical contact with the patient. One way to address this problem in the prior is to provide a "no touch" interval period prior to delivering the therapy shocks. However, this delay is undesirable as it delays the interval between the CPR precordial compressions and the delivery of defibrillation shock, thus preventing a quick response in administering a defibrillation shock which is vital in increasing the chance of surviving the cardiac arrest.

The above paragraph is not an accurate description of the prior art. First, let's distinguish between motion detection and artifact detection. Motion detection determines, via means of an external transducer or patient dependent parameter (e.g. transthoracic impedance), that the patient is being physically disturbed. It does not compare the disturbance signal to the patient's ECG to determine whether the motion has been manifested as corruption of the ECG signal. Artifact detection acquires a disturbance signal, which can be patient motion or any other possible source of ECG disturbance (e.g. electromagnetic), and compares it to the patient's ECG, e.g. by cross-correlation, in order to determine if the disturbance has manifested itself as corruption of the ECG. Such a corruption would make analysis of the ECG for shock advisory purposes unreliable, since the ECG is known to contain signals that are not of cardiac origin.

A typical AED therapy sequence following CPR is as follows:
1. Instruct rescuer "stop CPR", or "do not touch the patient."
2. Allow a short interval (e.g. 3 seconds or less) for the rescuer to discontinue CPR.
3. Begin acquiring ECG & disturbance signal for analysis.
4. Analyze an interval (e.g. 4.5 seconds) of ECG and disturbance signal. If motion is detected, repeat step 4, otherwise proceed to step 5.

5. If ECG analysis indicates VF or VT, begin charging therapy capacitor, At this point, the shock button is not armed, i.e. pressing it will have no effect.
6. Once capacitor is fully charged, arm the shock button and instruct the rescuer to press it.

The ForeRunner and FR2 (Philips) AED therapy sequence following CPR is as follows:
1. Instruct rescuer "do not touch the patient." Begin charging the therapy capacitor to an intermediate level (Philips patented precharge).
2. Allow a short interval (e.g. 3 seconds or less) for the rescuer to discontinue CPR.
3. Begin acquiring ECG & disturbance signal for analysis.
4. Analyze an interval (e.g. 4.5 seconds) of ECG and disturbance signal. If artifact is detected, repeat step 4, otherwise proceed to step 5.
5. If ECG analysis indicates VF or VT, finish charging therapy capacitor. At this point, the shock button is not armed, i.e. pressing it will have no effect.
6. Once capacitor is fully charged, arm the shock button and instruct the rescuer to press it.
1. The therapy sequence that we wish to protect is a follows: At a predetermined interval prior to the end of CPR, begin charging the therapy capacitor to an intermediate level (Philips patented precharge).
2. Instruct rescuer "stop CPR", or "do not touch the patient". Initiate final charging of therapy capacitor.
3. Allow a short interval (e.g. 3 seconds or less) for the rescuer to discontinue CPR.
4. Begin acquiring ECG & disturbance signal for analysis.
5. Analyze an interval (e.g. 4.5 seconds) of ECG and disturbance signal. If artifact and/or motion is detected, repeat step 5, otherwise proceed to step 6.
6. If ECG analysis indicates VF or VT, arm the shock button as soon as full charge is achieved (which may be immediately) and instruct the rescuer to press it. Otherwise, instruct "no shock advised."

An alternative embodiment is a follows:
1. Instruct rescuer "stop CPR", or "do not touch the patient". Immediately begin charging the therapy capacitor to full charge.
2. Allow a short interval (e.g. 3 seconds or less) for the rescuer to discontinue CPR.
3. Begin acquiring ECG & disturbance signal for analysis.
4. Analyze an interval (e.g. 4.5 seconds) of ECG and disturbance signal. If artifact and/or motion is detected, repeat step 4, otherwise proceed to step 5.
5. If ECG analysis indicates VF or VT, arm the shock button as soon as full charge is achieved (which may be immediately) and instruct the rescuer to press it. Otherwise, instruct "no shock advised."

In otherwords, the ideas that we wish to protect are:
Initiate full charge of the therapy capacitor prior to having knowledge as to whether we will recommend a shock or not. This may, or may not, be proceeded by pre-charging the capacitor.
Acquiring ECG and disturbance data during the capacitor charging operation (there is Philips prior art for this; both ForeRunner and FR2).
If ECG analysis indicates a heart rhythm deemed to be "shockable" (i.e. would benefit from electrical shock therapy), and a disturbance criteria is met, arm the defibrillator shock button immediately (with little or no delay to complete capacitor charging). Alternatively, the shock may be delivered automatically.
The disturbance criteria may be any of the following:
The absence of disturbance (e.g. motion), as determined solely from one or more disturbance signals
The absence of artifact, as determined by cross-correlation (or similar operation) of the ECG and one or more disturbance signals (Philips patented)
The absence of disturbance AND artifact.

In contrast, the present invention provides a defibrillation system in which the delivery of electrical therapy shocks is triggered by a combination of the detection of a treatable arrhythmia via an ECG analysis and a detection of the cessation or absence of CPR precordial compressions. Moreover, the inventive defibrillation system reduces the time interval between precordial compressions and a subsequent delivery of the defibrillation shock to less than 5 seconds. Furthermore, the inventive system detects the corruption of signals using a variable artifact analysis to determine an appropriate output level of the defibrillation shocks.

Figure 2:
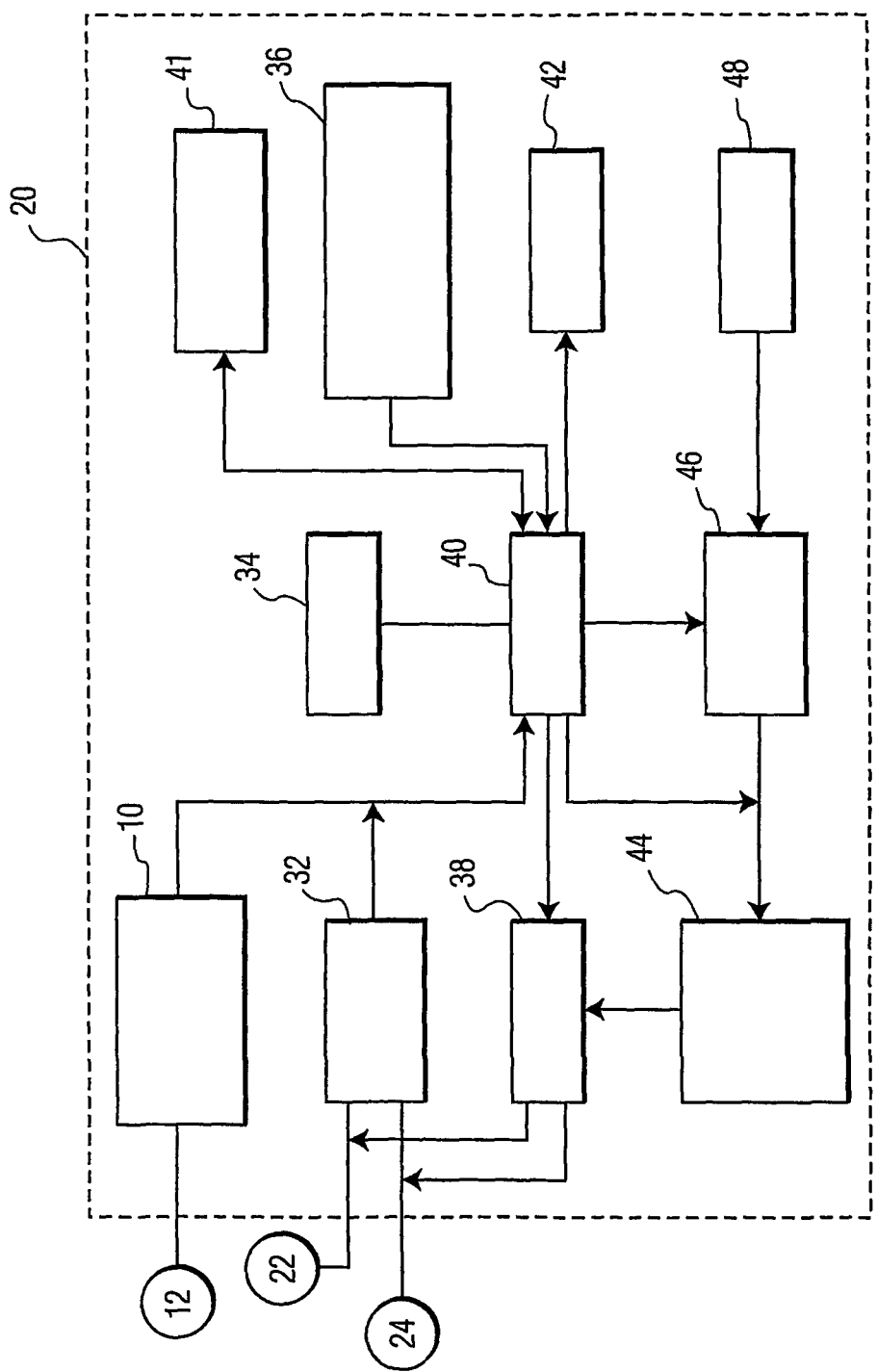
FIG. 2 depicts a representative hardware of the defibrillator illustrated in FIG. 1 according to an embodiment of the present invention.

FIG. 2 is a simplified block diagram of the defibrillator in accordance with the embodiment of the present invention. The defibrillator 20 may include a mechanical disturbance detector 10, an electrocardiogram (ECG) front end 32, a timer 34, a defibrillation activation/deactivation button 36, a HV switch 38, a processor 40, a display 42, an energy storage capacitor network 44, a voltage charger 46, and a battery 48. It should be noted that any number of commercially or publicly available defibrillator configured to generate a defibrillation shock can be utilized in various implementations in accordance with the preferred embodiment of the present invention.

As shown in FIG. 2, the mechanical disturbance detector 10 is connected to a sensor 12 that is placed on the patient to detect the movement of the patient during the delivery of CPR precordial compressions. The movement of the patient that may potentially corrupt the accurate assessment of the signal of interest is detected and forwarded to the processor 40. Similarly, the ECG front end 32 is connected to the electrodes 22 and 24 that are placed on the patient to amplify, filter, and digitize (using an analog to a digital converter) an electrical ECG signal generated by the patient's heart. The detected ECG samples are received by the processor 40, which runs a shock advisory algorithm for detecting VF or other shockable rhythm requiring treatment by the defibrillation shock. The ECG front end 32 is also capable of measuring the patient impedance across the electrodes 22 and 24 using a low-level test signal that is a non-therapeutic pulse to measure the voltage drop across the electrodes 22 and 24. The detected patient impedance is analyzed by the processor 40 to determine the appropriate energy level desired to be delivered to the patient. In an alternate embodiment, the function of the mechanical disturbance detector 10 and the ECG front end 32 can be merged as one component, such that one of the electrode connected to the ECG front end 32 may serve as a sensor for detecting the movement of the patient.

The HV switch 38 is configured to sequentially deliver the defibrillation pulse across the pair of electrodes 22 and 24 to the patient in the desired polarity and duration. It should be noted that the HV switch 38 could be adapted to deliver a single polarity (monophasic), both negative and positive polarities (biphasic) or multiple negative and positive polarities (multiphasic) in the preferred embodiment The timer 34 is connected to the processor 40 for providing a defibrillation pulse interval or duration when delivering the defibrillation pulse across the electrode pair 22 and 24. The activation/deactivation button 36 is connected to the processor 40 to enable the user to activate/deactivate the delivery of a defibrillation pulse across the electrodes 22 and 24 when the VF or other shockable rhythm is detected. Note that the activation/ deactivation button 36 can function in both AED and manual modes in the preferred embodiment. The voice circuit/speaker 41 is coupled to the processor 40 and provides voice instructions to the user during the operation of the defibrillator 20. The display 42, connected to the processor 40, is preferably a liquid crystal display (LCD) and provides audio and visible feedback to the user. The battery 48 provides power for the defibrillator 20 and in particular for the voltage charger 46, which charges the capacitors in the energy-storage capacitor network 44. The energy-storage capacitor network 44 includes a plurality of capacitors and resistors that are arranged in series or parallel arrangement, or a combination of series and parallel arrangement to supply a plurality of voltage-level outputs across the electrodes 22 and 24. It will be apparent to those skilled in the art that a variety of RC arrangements can be implemented to generate different voltage levels. In an alternate embodiment, the function of the energy-storage capacitor network 44 can be performed by functionally equivalent circuits, such as a digital-processor circuit or an application-specific integrated circuit (ASIC).

In operation, the electrodes 22 and 24 connected to the ECG front end 32 is placed on a patient for obtaining the patient impedance. The processor 40 uses the information received from the ECG front end 32 to control the shape of the waveform of the defibrillation pulse delivered to the patient in real time. The defibrillation pulse delivered to the patient may be a fixed level, or a number of defibrillation pulses at different energy levels. This can be achieved by selecting the appropriate voltage level of the energy-storage capacitor network 44 from the set of configurations to deliver the desired impedance-compensated defibrillation pulse to the patient.

When a rescuer performs chest compressions as part of doing CPR on the patient, the resulting chest movement tends to disturb the electrodes placed on the chest area. This is undesirable for detecting ECG signals as the movement of the electrodes on the chest skin area generates interfering electrical noise or artifacts, which may corrupts the ECG signal. As discussed in detail later, the artifact in the ECG signal caused by mechanical disturbances of sensors, electromagnetic interference, other environmental conditions, or artifact caused by movement due to the cardio-pulmonary resuscitation (CPR) operation are nevertheless useful as indicators that CPR is being performed, when CPR is concluded, and when the patient is being handled. An accelerometer or other motion sensor may be included in some embodiments for such detection purposes. As such, the sensor 12, such as an accelerometer that is connected to the mechanical disturbance detector 10 is also placed on the patient for detecting the patient's movement in response to the precordial compressions. The defibrillator 20 is also provided with the display 42 for visually indicating the shock annunciation, or may be equipped with a voice circuit and speaker 41 for providing audible announcement just prior to delivering the defibrillation shocks.

Note that during the rescue attempt, if renewed mechanical disturbance is detected, the defibrillation activation/deactivation 36 is provided for cancellation of the shock within the brief delay interval prior to therapy deliver. Alternatively, the motion of new mechanical disturbance can be detected automatically and cause the cancellation of the defibrillation shock therapy.

Figure 3:
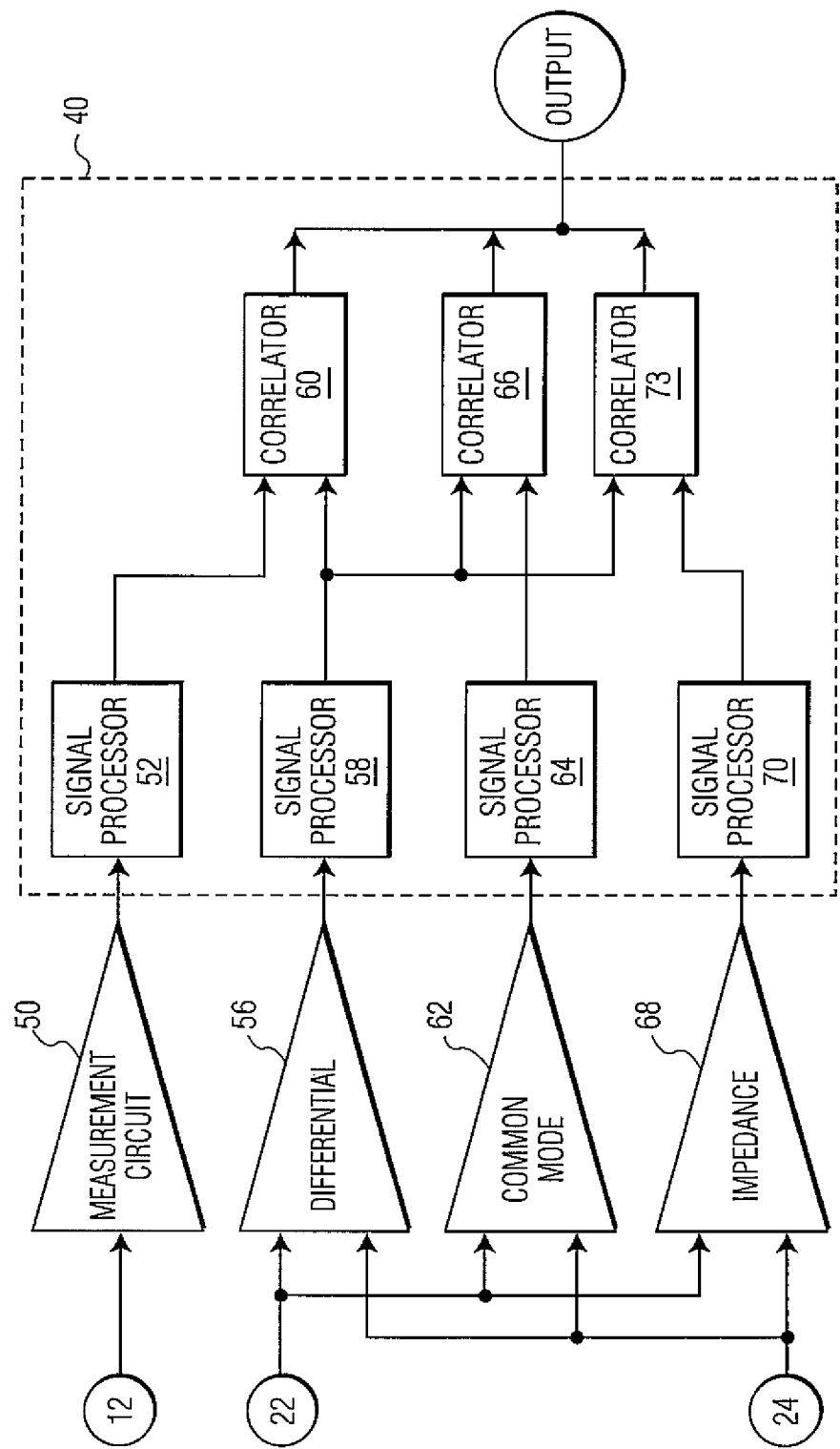
FIG. 3 is a diagram of the hardware configured to deliver an artifact-compensated defibrillation shock according to an embodiment of the present invention; and, FIG. 4 is a flow chart illustrating the operation steps of the defibrillation system in accordance with the present invention.

FIG. 3 is a detailed description of the components that enable a rapid analysis during mechanical disturbances, so that arrhythmia determination can be made using artifact-free ECG following the cessation of mechanical disturbance. Note that detecting artifact can be performed in a variety of ways. For example, signal processing and correlation of processed signals in accordance with the present invention may include various embodiments described in U.S. patent application Ser. No. 6,287,328, filed by the applicant and issued on Sep. 11, 2001, entitled "Multivariable Artifact Assessment," the teachings of which are incorporated herein by reference.

Briefly, an input signal indicative of patient movement is received via the sensor 12 and provided to the measurement circuit 50. The signal is then sent to a signal processor 52 and forwarded to a correlator 60, and the correlated signal is processed by the processor 40. The processor 40 then evaluates the signals to produce an output signal. As will be appreciated by those skilled in the art, an appropriate signal processing includes, for example, band-pass filters, Fourier transforms, wavelet transforms, and joint time-frequency spectrograms. In addition, the method for correlating the data can be any correlation method known in the art. For example, correlation methods include specific and general cross-correlation techniques, which include known mathematical functions as well as any process that effectively correlates the data. Specific implementations include, but are not limited to, finite sampled or continuous estimates of cross-covariance and cross-correlation, both biased and unbiased. Alternatively, correlation may perform similarity comparisons between any multiple signals.

Meanwhile, an input signal indicative of the patient impedance is received across the electrodes 22 and 24 and transmitted to a differential-mode amplifier 56 and a common-mode amplifier 62 which amplify the signal prior to transmitting the signal to the signals processors. The resulting signals are then transmitted to their respective signal processors 58 and 64 which process the signals to emphasize particular features. The resulting processed signals are then transmitted to a correlator 66, which correlates the signals. At the same time, the input signal is transmitted to impedance detector 68, which provides a trans-electrode impedance signal to a signal processor 70. Signal processor 70 processes the signal from the impedance detector 68 to emphasize particular features of the signal. The resulting processed signal is then transmitted to a correlator 73, which correlates the signal from signal processor 70 with the processed signal from the differential amplifier signal processor 58. Once the signals have been correlated at their respective correlators 60, 66 and 73, the resulting signals are processed by the processor 40, which then further evaluates the results of the correlators 60, 66 and 73 to provide an indication of the degree of corruption of the signal of interest. The processor 40 finally provides an output signal, which may be analyzed further as discussed with respect to FIG. 4 below.

Figure 4:
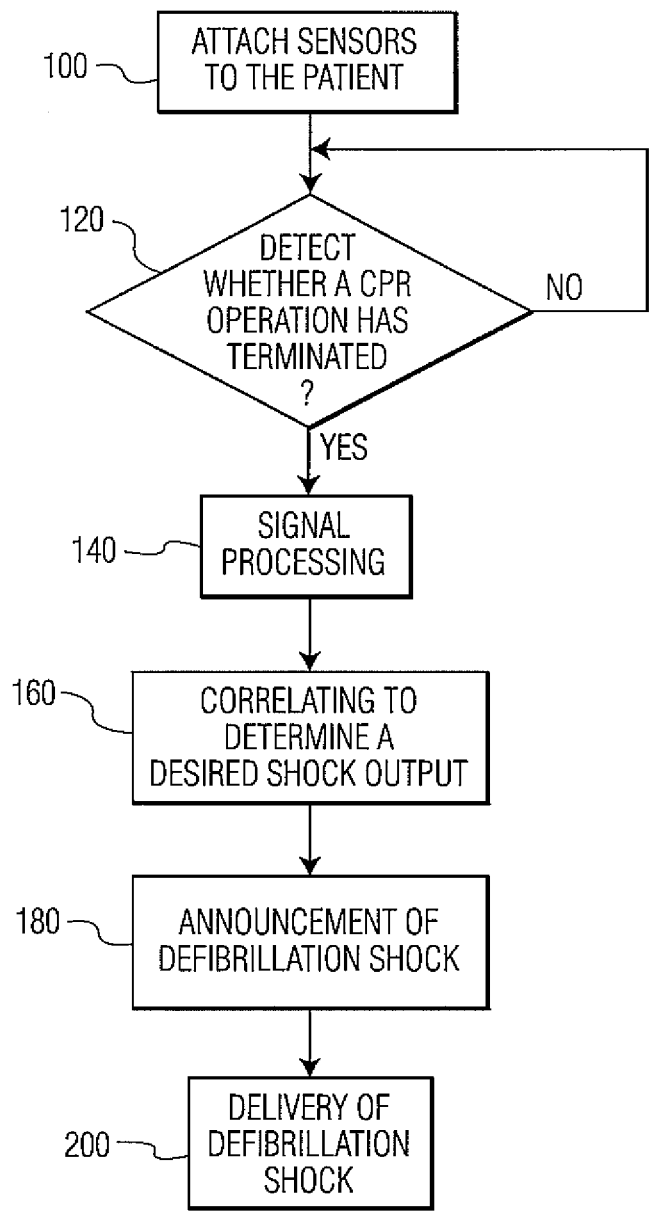

FIG. 4 is a flow chart illustrating the operation steps of delivering an artifact-compensated defibrillation shock while administering a CPR treatment according to the present invention. Initially, the inventive defibrillator 20 is deployed in step 100 by attaching the sensor 12 and the electrodes 22, 24 to the cardiac victim to analyze a patient input signal. The input signal due to potentially corrupted signal and/or the movement of the patient during a CPR operation is detected. Note that it is common to perform CPR precordial compressions on the victim in conjunction with the use of the defibrillator during rescue attempts. As such, in step 120, the system 20 determines whether a CPR operation has stopped using the input signal from the sensor 12 in step 120. If so, the electrodes 22 and 24 connected to the ECG front end 32 detect an input signal, i.e., ventricular fibrillation (VF) and the patient impedance is measured by measuring a low-level test signal or delivering a non-therapeutic signal in step 140.

Thereafter, the signal processing is implemented in order to emphasize a particular feature of the data in the input signal in step 160. Here, various implementations of processing, including known techniques such as filters, Fourier transforms, wavelet transforms, and joint time-frequency spectrograms, are employed. For example, the lower spectral portion of a Fourier transform of an ECG signal might be correlated with a similarly processed impedance signal in order to enhance the detection of an artifact resulting from a defibrillator operator performing CPR on a patient being monitored. Accordingly, the correlating step 160 performs the function of measuring similarities between the processed cardiac signal and the processed corrupted signals.

The resulting comparisons are then analyzed to determine an indication of the amount of artifacts present within the potentially corrupted cardiac signal.

The result of the comparisons is processed by the processor 40 in order to determine the level of the defibrillation shock, which may include a series of successive defibrillation shocks at a predetermined interval, to be delivered to the patient. The energy level may be determined by the operator manually, or it can be determined by automatically utilizing a common protocol known in the art. Here, the processor 40 also determines the polarity and duration of the defibrillation shock. After determining the desired energy level output, the processor 40 sends a notification signal to the user in step 180 prior to delivering the defibrillation shock. At the same time, the processor 40 sends a signal to the HV switch 38 to actuate the switches to discharge the desired defibrillation shock to the patient. Alternatively, the processor 40 may notify the operator via the display 42 to press the shock button 36 to actuate manually the delivery of the defibrillation shock to the patient. Finally, the defibrillation shock is discharged to the patient in step 200, then the patient's heart is monitored to determine whether a subsequent defibrillation shock is necessary. If so, the above steps may be repeated to deliver the subsequent defibrillation shock.

While the preferred embodiments of the present invention have been illustrated and described, it will be understood by those skilled in the art that various changes and modifications may be made and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

The invention claimed is:

1. A method for delivering a defibrillation shock using a defibrillator, the method comprising the steps of:
    (a) having the defibrillator initiate a cardio-pulmonary resuscitation (CPR) interval;
    (b) prior to an end of the cardio-pulmonary resuscitation (CPR) interval, analyzing the ECG signal for signal corruption and, if a cessation or absence of CPR precordial compressions is indicated by substantially no signal corruption;
    (c) analyzing an ECG signal prior to the end of the originally initiated cardio-pulmonary resuscitation (CPR) interval to determine if a defibrillation shock is needed; and,
    (d) delivering a defibrillation shock if the analyzing step (c) indicates that a defibrillation shock is needed.

2. The method of claim 1, wherein step (c) includes charging the defibrillator prior to the end of the originally initiated cardio-pulmonary resuscitation (CPR) interval.

3. The method of claim 1, wherein step (c) includes determining whether a disturbance associated with the cardio-pulmonary resuscitation (CPR) interval is detected; and, if there is substantially no disturbance, delivering the defibrillation shock if needed.

4. The method of claim 1, further comprising the step of notifying an operator of the defibrillator prior to delivering the defibrillation shock.

5. The method of claim 1, wherein the defibrillation shock is provided about 10 seconds or less after the cessation of precordial compressions.

6. A method for delivering a defibrillation shock using a defibrillator, the method comprising the steps of:
    prompting a start of a CPR therapy interval;
    detecting an indication of CPR precordial compression cessation during the CPR therapy interval; and,
    arming the AED for defibrillation shock delivery based on the detected cessation of precordial compressions detected during the CPR therapy interval.

7. The method of claim 6, wherein the arming step is complete in less than about 10 seconds from detection of the cessation of precordial compressions.

8. The method of claim 6, wherein the indication is based upon a predetermined end of the CPR therapy interval.

9. The method of claim 8, wherein the arming step includes initiating a charging of the high voltage energy source prior to the predetermined end of the CPR therapy interval.

10. The method of claim 8, wherein the arming step includes completing a charging of a high voltage energy source of the defibrillator prior to the predetermined end of the CPR therapy interval.

11. The method of claim 8, further comprising the steps of:
    obtaining an ECG signal from the ECG detector prior to the predetermined end of the CPR therapy interval; and
    determining whether the ECG signal is corrupted by CPR activity, wherein the arming step is further based on determining an uncorrupted ECG signal.

12. The method of claim 6, wherein the indication of CPR cessation includes a signal generated by CPR activity.

13. The electrotherapy method of claim 12, further comprising the steps of:
    obtaining an ECG signal from the ECG detector prior to the CPR cessation; and
    determining whether the ECG signal is uncorrupted by CPR activity; wherein the arming step is further based on the determining step.

14. A method for delivering a defibrillation shock using a defibrillator, the method comprising the steps of:
    coupling a plurality of sensors to the patient's body to detect physiological signals of the patient;
    initiating a predetermined CPR therapy interval during which precordial compressions are to be administered to the patient;
    monitoring a physiological signal received from at least one of the sensors to detect a cessation of precordial compression administration prior to the end of the predetermined CPR therapy interval;
    upon detecting a cessation of precordial compression administration prior to the end of the predetermined therapy interval, obtaining ECG signals from a plurality of the sensors;
    analyzing the obtained ECG signals to determine whether a defibrillation shock is needed; and
    if the analyzing step determines that a defibrillation shock is needed, delivering a defibrillation shock to the patient through a plurality of the sensors.

15. The method of claim 14, wherein one of the sensors detects a signal indicative of patient movement due to CPR motion,
   wherein the signal indicative of patient movement is used in the detecting step.

16. The method of claim 14, wherein one of the sensors detects a signal indicative of ECG signal corruption from CPR activity,
   wherein the signal indicative of ECG signal corruption is used in the detecting step.

17. The method of claim 14, further comprising the step of initiating charging of a high voltage energy source prior to the predetermined end of the predetermined CPR therapy interval.

\* \* \* \* \*